US009529968B2

(12) United States Patent
Adams

(10) Patent No.: US 9,529,968 B2
(45) Date of Patent: Dec. 27, 2016

(54) SYSTEM AND METHOD OF INTEGRATING MOBILE MEDICAL DATA INTO A DATABASE CENTRIC ANALYTICAL PROCESS, AND CLINICAL WORKFLOW

(71) Applicant: Cernoval, Inc., Sammamish, WA (US)

(72) Inventor: Bruce William Adams, West Vancouver (CA)

(73) Assignee: CERNOVAL, INC., Sammamish, WA (US)

(*) Notice: Subject to any disclaimer, the term of this patent is extended or adjusted under 35 U.S.C. 154(b) by 45 days.

(21) Appl. No.: 14/046,942

(22) Filed: Oct. 5, 2013

(65) Prior Publication Data

US 2014/0100878 A1    Apr. 10, 2014

Related U.S. Application Data

(60) Provisional application No. 61/710,737, filed on Oct. 7, 2012.

(51) Int. Cl.
*G06Q 50/00* (2012.01)
*G06F 19/00* (2011.01)

(52) U.S. Cl.
CPC .......... *G06F 19/322* (2013.01); *G06F 19/321* (2013.01); *G06F 19/3437* (2013.01)

(58) Field of Classification Search
None
See application file for complete search history.

(56) References Cited

U.S. PATENT DOCUMENTS

| | | | | |
|---|---|---|---|---|
| 6,152,822 A * | 11/2000 | Herbert | ............... | G07F 17/32 463/16 |
| 6,606,615 B1 * | 8/2003 | Jennings | ............... | G06Q 10/06 706/45 |
| 7,730,063 B2 * | 6/2010 | Eder | ............... | G06F 19/3437 705/2 |
| 8,126,728 B2 * | 2/2012 | Dicks | ............... | A61B 5/0022 600/300 |
| 2004/0078220 A1 * | 4/2004 | Jackson | ............... | G06F 19/327 705/2 |
| 2009/0131132 A1 * | 5/2009 | Kohls | ............... | G06Q 10/06 463/6 |
| 2009/0132276 A1 * | 5/2009 | Petera | ............... | G06Q 50/22 705/2 |
| 2010/0274589 A1 * | 10/2010 | Bauer | ............... | G06F 17/30914 705/3 |
| 2011/0029326 A1 * | 2/2011 | Venon | ............... | G06Q 10/06 705/3 |
| 2011/0202572 A1 * | 8/2011 | Ho | ............... | G06F 19/322 707/802 |
| 2011/0238437 A1 * | 9/2011 | Zhou | ............... | G06F 19/3487 705/2 |

(Continued)

*Primary Examiner* — Sunit Pandya

(57) ABSTRACT

The present invention provides a system and method of integrating mobile medical data into a database centric analytical process, and clinical workflow. This includes a method comprising: integrating smartphone and digital camera data into a clinical database management system comprising a database association and a clinical workflow based on a per dictum, including clinical session and procedural data and metadata, and generally involving shared communication of text data, and photographic and video/audio data sets associated with a patient file through a secured workflow series.

8 Claims, 18 Drawing Sheets

The stakeholders in a clinical support database environment.

(56) References Cited

U.S. PATENT DOCUMENTS

| | | | |
|---|---|---|---|
| 2011/0307274 A1* | 12/2011 | Thompson | G06F 19/327 705/3 |
| 2012/0173278 A1* | 7/2012 | Herbst | G06Q 10/10 705/3 |
| 2015/0032464 A1* | 1/2015 | Vesto | G06F 19/345 705/2 |

* cited by examiner

FIGURE 1

| |
|---|
| Biomechanical Video Protocol Example |
| Measure as follows: |
| 1.0 Resting posture; ask patient to sit at rest, gently holding their teeth together. |
| 1.1 The occluded resting posture; sagittal view; then translate to protrusive and back to normal. [5-10 seconds of video] |
| 1.2 The occluded resting posture; frontal [still photo or short video] |
| 2.0 Disengaged rest position: after recording the prior frontal view, and with the video recording, ask the patient to allow their teeth to separate with a comfortable space between the them. frontal [5-10 seconds of video] |

A sample of a protocol to assist a clinician to use a mobile device in a clinical workflow.

FIGURE 2

| Range of Motion : | |
|---|---|
| | Mandibular Open / Close |
| | Protrusive |
| | Cranial / Facial / Cervical |
| | Frequency analysis |
| Occlusograms : | |
| | Freeway, |
| | Contact Deviations, kinematic protrusive and lateral |
| | | an example of a drop down menu on a smart phone menu that a clinician would use to select the procedures that would set a session with a database and external online laboratory services.

FIGURE 3

| 524.63 | TMJ Disk Disorder |
|--------|--------------------|
| 719.4  | Bilateral TM Joint Pain |
| 715.2  | Osteoarthritis (chronic) degenerative TMJ |
| 715.28 | Osteoarthritis, localized, secondary |
| 718.89 | Unspecified disorder of muscle, ligament and fascia |
| 723.1  | Cervicalgia |
| 728.85 | Spasm of Muscle |
| 729.2  | Neuralgia, Neuritis, facial |
| 780.4  | Dizziness, vertigo |
| 781.0  | Trismus |
| 784.0  | Head and/or Neck Pain |
| 959.0  | Trauma to head/neck |

An example of billable procedures from a drop down menu on a smart phone that a clinician would use to select the procedures that would begin a session with a clinical support database and external online laboratory services.

The features of mobile computing means including digital cameras, smartphones, and personal computers that may be used in a clinical environment to communicate with a clinical support database and third party providers.

The stakeholders in a clinical support database environment.

The features of the clinical support database environment.

A sample of the clinical procedures, protocols, sequences and per dictum and workflow associated with a clinical support database.

The clinical login procedures including patient identification.

The clinical session procedures of the presentation layer, including session workup and protocols The session workflow including per dictum, service engagement, report generation, and database and workflow updates.

A smart phone with a icon and visual notification of results to download and or read.

A workflow progression on a smartphone that indicates the progress of various patient files, showing updates from a clinical support database.

Data analysis for session data, procedural conditions, clinical events and modeling.

The analysis system that enables the database to use iterative learning in processing and storage of session data and metadata.

illustrates the presentation layer where an interactive workflow will call up specific tasks such as required process to capture digital images Presentation layer showing probability analysis to allow for direct interface to the data, or allowing the clinician to change the weighting of certain parameters to force the system to recalculate the probability of other conditions. In the interface color is used to help differentiate quickly.

A presentation layer that enables the choice of a processing algorithm for report generation.

SYSTEM AND METHOD OF INTEGRATING MOBILE MEDICAL DATA INTO A DATABASE CENTRIC ANALYTICAL PROCESS, AND CLINICAL WORKFLOW

CROSS-REFERENCE TO RELATED APPLICATIONS

This application claims benefit under 35 U.S.C. 119(e) to U.S. provisional patent application Ser. No. 61/710,737, filed Oct. 7, 2012, which is incorporated herein by reference in its entirety.

BACKGROUND

Field of the Invention

The present invention pertains to the field of medical data analysis and in particular to the use of mobile imaging and data technology in a clinical environment.

Description of Related Art

Recent use of smart phones, tablets, digital cameras and portable media has rapidly enabled clinical service providers to capture and save images and other data such as text in a format used more generally for non professional photography or social media. As a result apriori existing standards in privacy and security are often being ignored in order to enable rapid and simple data capture in a clinical environment.

For instance, the dominant apriori standard for radiology imaging and communication is Digital Imaging and Communications in Medicine ("DICOM"). DICOM standardizes the data format and transfer protocol for data such as images, waveforms, workflow messages and diagnostic reports. It is used in many fields of medicine, such as for example, radiology, cardiology and dentistry. The DICOM standard encompasses a large number of medical imaging modalities, such as computed tomography, magnetic resonance, ultrasound, and digital radiography. The standard assumes that the application entities involved in a DICOM interchange are implementing appropriate security policies, including, but not limited to access control, audit trails, physical protection, maintaining the confidentiality and integrity of data, and mechanisms to identify users and their rights to access data. Essentially, each application entity must insure that their own local environment is secure before even attempting secure communications with other application entities.

However the use of present art smart phones, digital cameras, personal computers and social media present art does not allow for these devices to be used to existing standards of patient rights, and further present methods fall well short of analytical capability that could be used by clinicians to patient benefit.

Present methods can store medical images, waveforms and diagnostic reports including metadata along with content. The metadata can augment the content with ownership, organization, imaging condition, layout, and workflow information. There is frequently a need to search medical data using its metadata or share the metadata in a variety or database formats. For instance, XML is widely used in metadata management applications. However these methods have rarely been combined with advanced analytics such as predictive measures nor with real time analytics.

It would therefore be advantageous to be able to secure mobile data in a clinical environment and further guide clinicians in using these mobile devices to ensure the best practices.

This background information is provided to reveal information believed by the applicant to be of possible relevance to the present invention. No admission is necessarily intended, nor should be construed, that any of the preceding information constitutes prior art against the present invention.

SUMMARY OF THE INVENTION

An object of the present invention is to provide a system and method of integrating mobile medical data into a database centric analytical process, and clinical workflow. In accordance with one aspect of the present invention, there is provided a method comprising the integration of smartphone and digital camera data into a clinical database management system comprising a series of database associations that are defined by a clinical workflow based on a per dictum, including clinical session data, clinical session metadata, procedural sequence metadata, including a communication attribute and a procedurally specific attribute that further defines the relationships of metadata associated within a corresponding workflow series.

In accordance with another aspect of the present invention, there is provided a system and method of integrating smartphone and digital camera data into a clinical database management system comprising an output from the support services database as combined with procedural sequences to create a display and documentation series within a corresponding workflow series.

BRIEF DESCRIPTION OF THE FIGURES

FIG. 1 illustrates a sample of a protocol to assist a clinician to use a mobile device in a clinical workflow.

FIG. 2 illustrates an example of a drop down menu on a mobile device menu that a clinician would use to select the procedures that would set a session with a database and external online laboratory services.

FIG. 3 illustrates an example of billable procedures from a drop down menu on a mobile device that a clinician would use to select the procedures that would begin a session with a clinical support database and external online laboratory services.

DETAILED DESCRIPTION OF THE INVENTION

Definitions

The term "per dictum" is used to define the action taken by a clinician to initiate a clinical session with a smartphone, or digital camera or the like, where such action will involve a database management system, similar in intent to a traditional prescription, however, referring more exclusively to the use of digital mobile solutions described herein, to provide a care workflow.

The term "clinical session data" is used to define the data captured during a clinical session, or the models of prior clinical session data as might be processed for normalizing purposes for a general demographic of people, or for an individual patient, such data including but not limited to text, video, audio, images and accelerometer data for either pre clinical screening or actual clinical procedures.

The term "clinical session metadata" is used to define either or both the real time descriptive data from a device, or post processed data associated with procedures such as predictive or iterative data, all which could be used to characterize the clinical session.

The term "procedural sequence metadata" is used to define the various procedures including clinical guides, procedures codes, billing codes, clinician data, and patient data as might be associated to a per dictum for clinical services or a clinical session and enable uploading, post processing, data queries and searches, downloading and report generation.

The term "clinician" is used to define a person authorized to provide services in a clinical or related environment.

The term "presentation layer" is used to define the user interface that incorporates, based on the per dictum, some combination of the clinical session data, clinical session metadata, procedural sequence metadata, supported by a clinical support database, such that a standard format of data can be represented that enables an iterative interface.

As used herein, the term "about" refers to a +/−10% variation from the nominal value. It is to be understood that such a variation is always included in a given value provided herein, whether or not it is specifically referred to.

Unless defined otherwise, all technical and scientific terms used herein have the same meaning as commonly understood by one of ordinary skill in the art to which this invention belongs.

Figure 4:
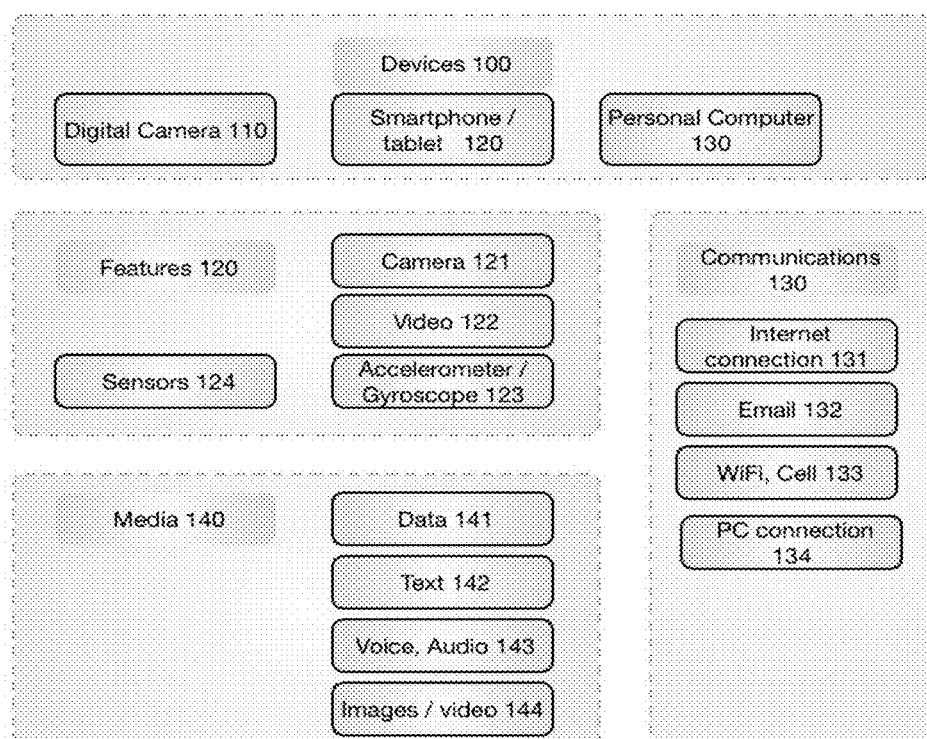
FIG. 4 illustrates the features of mobile computing means including digital cameras, smartphones, and personal computers that may be used in a clinical environment to communicate with a clinical support database and third party providers.
Figure 5:
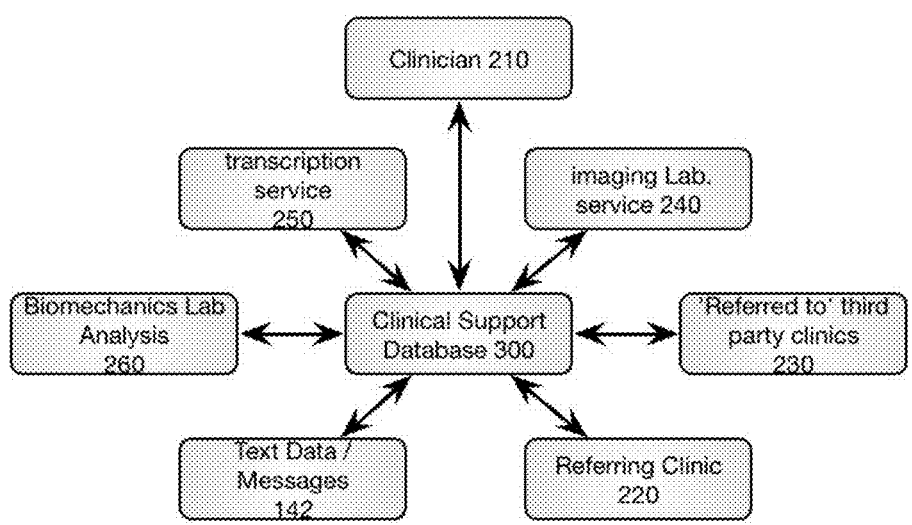
FIG. 5 illustrates the stakeholders in a clinical support database environment.

The present invention provides a mobile media data input FIG. 4, or other interface system, network connection, and supplementary metadata, to capture data to a post processing procedure from a clinical or pre-clinical environment. A software process allows for user inputs of data in accordance to apriori established methods and rules.

Figure 8:
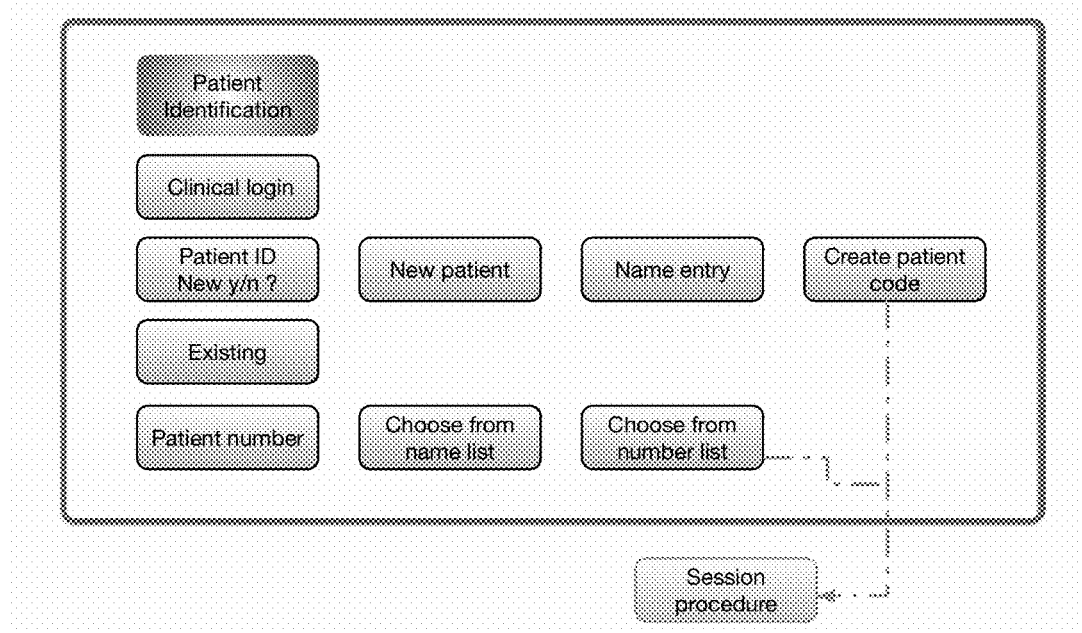
FIG. 8 illustrates the clinical login procedures including patient identification.
Figure 9:
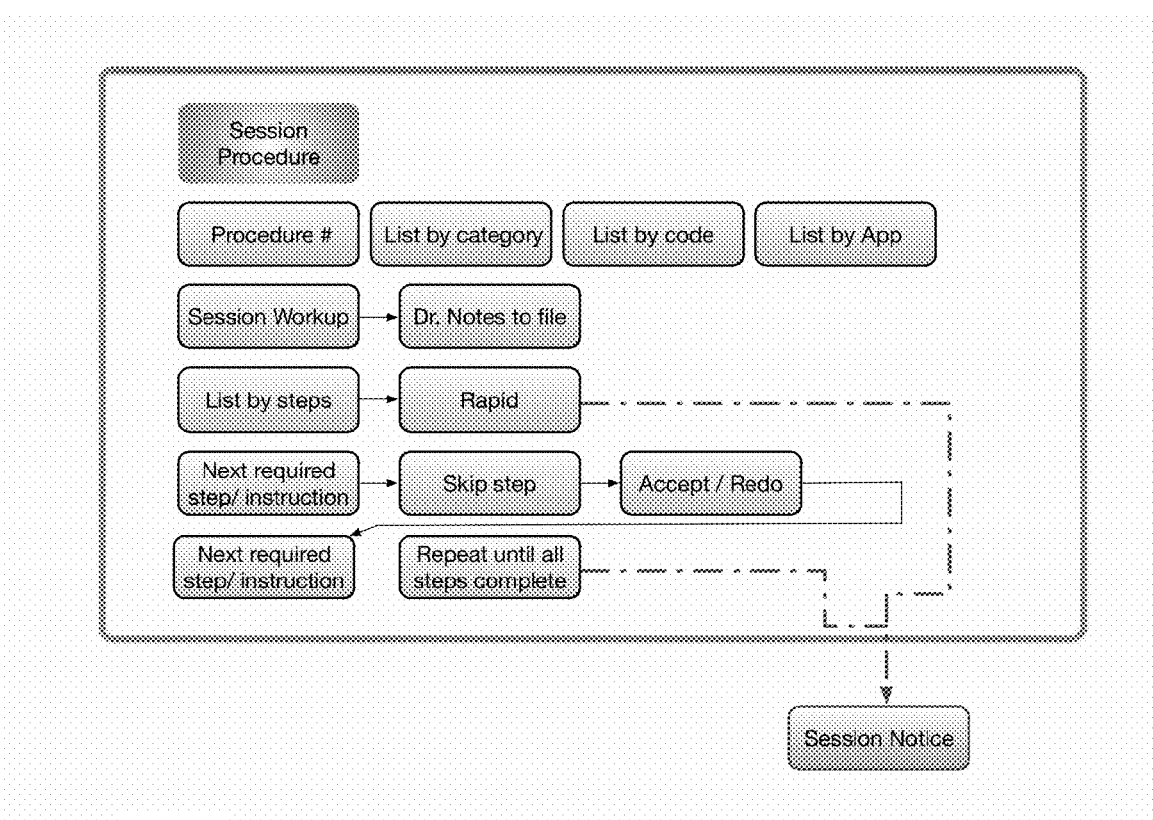
FIG. 9 illustrates the clinical session procedures of the presentation layer, including session workup and protocols.

The disclosed embodiments are directed to a system and method of integrating mobile medical data from the group of mobile devices including smartphones, tablets, network connected sensors and digital cameras into a database and clinical workflow, including a method of integrating a session of photographic images, text, audio, such as voice, video, accelerometer and other data captured in a clinical environment into a database management system. The clinical session data is initiated or authorized by the clinician and creates provider data, the patient specific data, the session data, the per dictum details, and associated with the clinical session metadata, procedural sequence metadata, service provider communications and reports, in a workflow, FIGS. 8, 9, 10, that updates the clinical provider in the presentation layer with the various changes of data, post processed data or report status. In some cases the clinical session data can be acquired from the patient using a screening interface prior to the actual clinical visit with the clinician. Such screening interface could be enabled on a dedicated device or a web interface.

Figure 6:
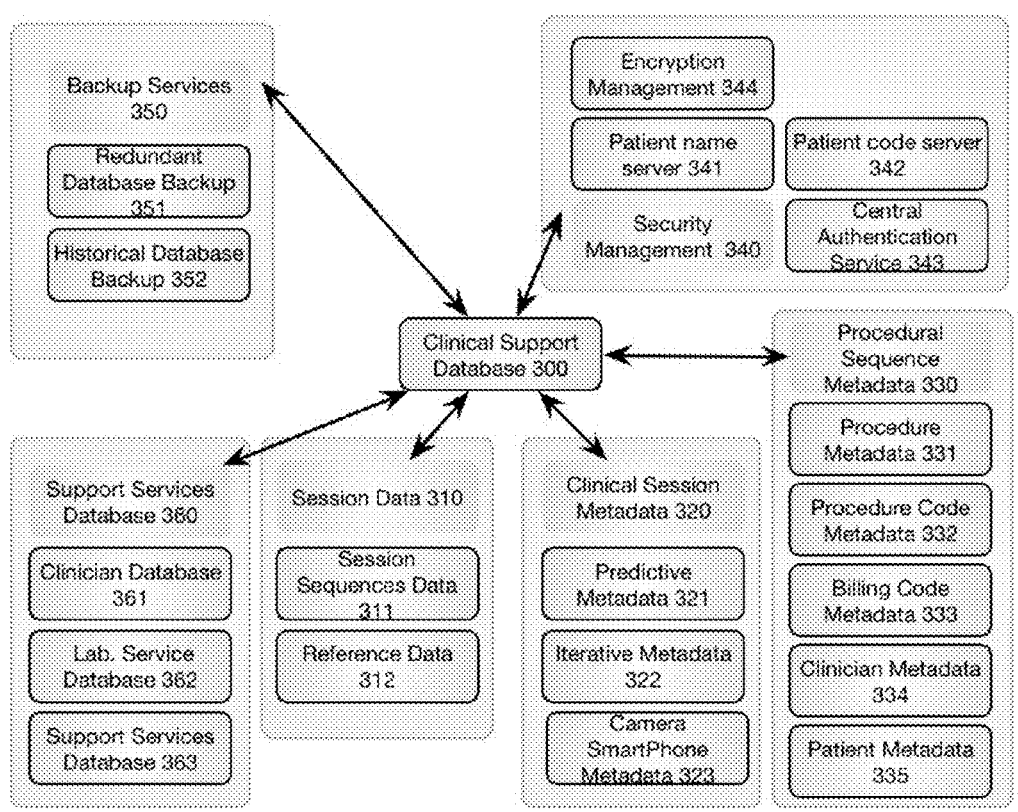
FIG. 6 illustrates the features of the clinical support database environment.
Figure 7:
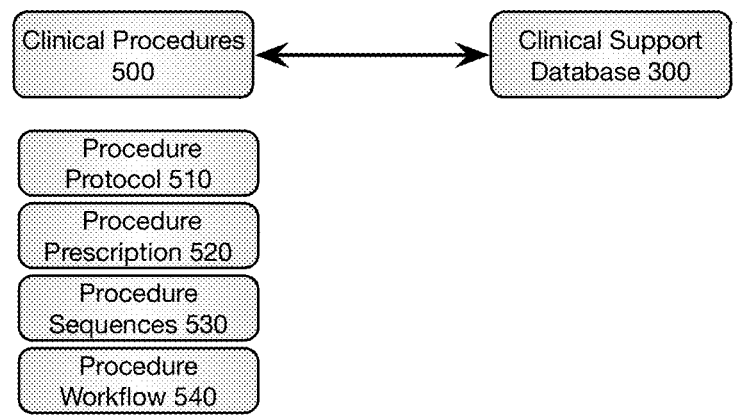
FIG. 7 illustrates a sample of the clinical procedures, protocols, sequences and per dictum and workflow associated with a clinical support database.

A data session is characterized by the requirements of a complete database support structure FIG. 6 including provider data, the patient data, the session data, the per dictum, service provider communications and reports, in a workflow that updates the clinical provider by way of a presentation layer, of the data or report status.

In one embodiment, a clinical session opens a database session where a table is created and a database object is initialized with a clinical image session including patient specific data and the associated metadata. The clinical image data is parsed and a JSON, or the like, representation of metadata associated with the clinical image data is created and the database object is inserted in the table. The clinical data session presentation layer can be created or opened and viewed with a mobile computer, or other interface such as a personal computer, as would be known to one skilled in the art. The presentation layer includes the outcomes of associating clinically defined attributes and procedurally defined attributes and mapping session data including workflow into the database.

DETAILED DESCRIPTION

The clinical session data 310 is the media 140 as collected by using mobile devices 100 including but not limited to digital cameras 110, smartphones or tablets 120, or personal computers 130, that can be used as an adjunct to clinical procedures and communications using their features 120 including one of the group of cameras 121, video features 122, accelerometer/gyroscope 123, or other sensors, attached to the mobile platform or acting as an independent mobile platform 124. These devices collect or create or share data 141, text 142, voice and audio 143, still and video images 144 and system metadata 323. These features are then shared by communication 130 in public or private networks including the internet 131, email 132, WiFi, Cellular 133, or to a PC connection 134 which might be connected to other means independently. Clinical session data can consist of session sequences data 311 providing a time domain correlation for normalization, and reference data 312, that would enable comparative features for data comparison. Clinical metadata is the set of attributes extracted, derived or annotated from clinical data that are needed to describe a patient information session, and its associated workflow, including describing the clinical data 310, clinical metadata 320, procedural data 330 and associated metadata as an objects in a database, where they can be further organized and retrieved.

Mobile media devices such as the smartphone 120, tablet and digital camera 110, and other computers such as desktop and laptop computers can be used to create and share data related to a clinical workflow. For instance an iPhone smartphone can collect image, video, voice, gyroscope and accelerometer data and this data can be used independently or combined in special procedures in a clinical workflow.

These variable data sources can be used in a patient session where a sequence of prescribed images FIG. 1 or other data, can be combined in a logical format and represented for the purposes of database organization, as a dependent object series, that include the variable and non variable support components of the presentation layer including clinical procedures 500, and procedures for clinical protocols 510, per dictum protocol 520, procedure sequences protocol such as a guide to follow steps in a timeline, and procedure workflow protocol 540, such as screening results interpretation and follow up steps. In this regard the database also includes fixed and variable components that are based on the per dictum. Variable components can also be defined by post processing requirements, including for instance the variable requirements for biomechanical studies using video analysis, or for lesion analysis using single or multiple images. Clinical session metadata 320 and procedural sequence metadata 330 can be associated with a session and could include procedure codes 332, billing codes 333, clinician metadata 334, patient metadata 335, or other identifying components such as a sequence number in a protocol of imaging techniques, indexed in the database.

In a workflow, metadata can be used to improve communications between clinicians, patients and laboratories, and can for instance be used to manage a clinical session. To open a session a clinician would log-in to verify credentials and account verification, verify patient identification and associated patient codes, assure that image and data authorizations are valid, such as imaging consent to assure privacy rules are met with authorization from a patient, especially where photograph, or audio or video recordings of patients for treatment or otherwise could disclose a patients identification FIG. 8. Such patients' written authorization, or clinician log-in can be obtained in either a paper or paperless format on a mobile device including patient specific codes such as an insurance ID number or biometrics such as fingerprint scans or iris scans. Patient names may not be a mandatory part of the database, but may be used to improve workflow. Names can be entered into the searchable patient metadata and would be entered into a clinicians record and would update the web interface/smartphone interface. This could include uploading data from a third party database. In one embodiment of the invention, there are three servers that are used to enable security 340 on the mobile platforms, including a patient name server 341, a patient code server 342, a central authentication service 343, and encryption management 344, together or individually can provide functions to enable security privileges, while at the same time reduce the vulnerability of private data to unauthorized parties all of which would be known to one skilled in the art. In a smartphone environment clinicians would be able to associate clinical files such as images created with their camera and smartphone systems with other existing patient records, including exporting reports or images to a third party database. In such a case export utilities could be required to parse the data to allow for the transfer of session data or metadata.

Figure 16:
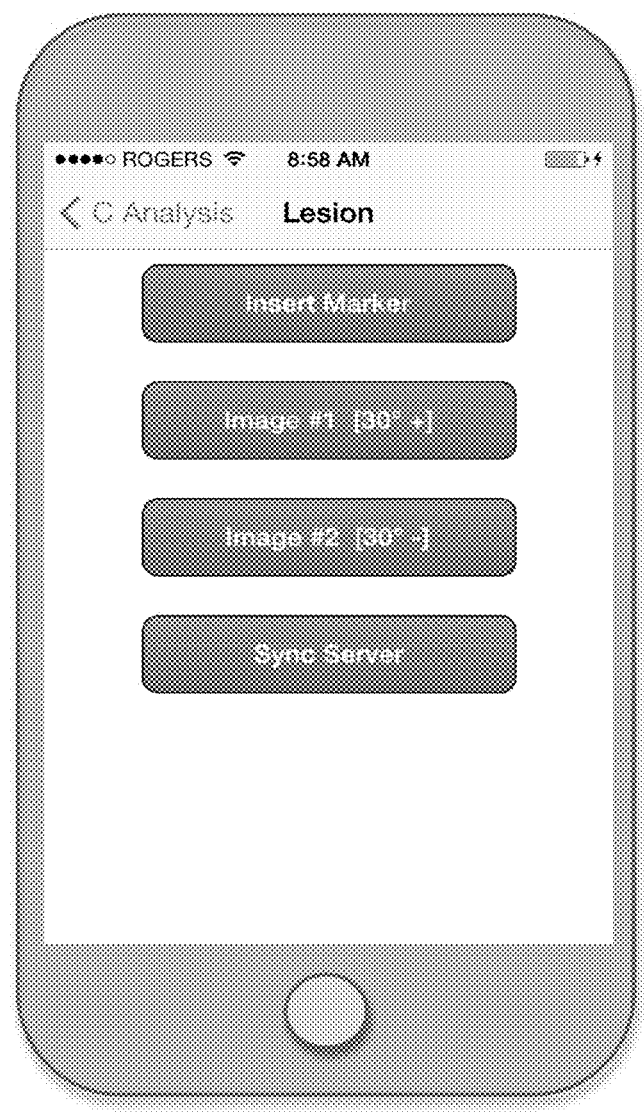
FIG. 16 illustrates the presentation layer where an interactive workflow will call up specific tasks such as required process to capture digital images.

Session metadata 320 can be matched to a patient profile database based on prescribed clinical procedures and protocols, image processing parameters and requirements. For example, a clinical procedure FIG. 2, may correspond to a clinical sequence of tasks and describe a technique for capturing images. A patient specific session procedure number and a list of procedures and codes will be available from a drop down menu on a smartphone, or alternatively a choice of application specific smartphone 'apps' with required procedures, which can be made available to a clinician or procedures can be defined as associated with billing or procedure codes FIG. 3. The presentation layer includes an interactive workflow where some procedures FIG. 9, will call up specific tasks such as required images and allow a clinician to adjust for empirical experience such as to skip, accept or redo an image, or request advice from an iterative system 322 such as image augmentation with multiple images to improve resolution or improve spectral signal to noise ratios with an array of matched filters as would be known to one skilled in the art. For example, in one embodiment, such a workflow could require images from different angles and the confirmation of this, FIG. 16. An image file series could also be created without the guided workup in a rapid format, by an experienced clinician where the number of images could be combined using metadata, such as with their know orientation from accelerometer data. The real time angles and relationships could be presented in the presentation layer to help guide the image collection. An input image will be associated with a procedural sequence 330 in the database. Additional metadata may then be added to, or retrieved from the session data or its database profile in order to perform processing directly associated with the per dictum 520.

Figure 10:
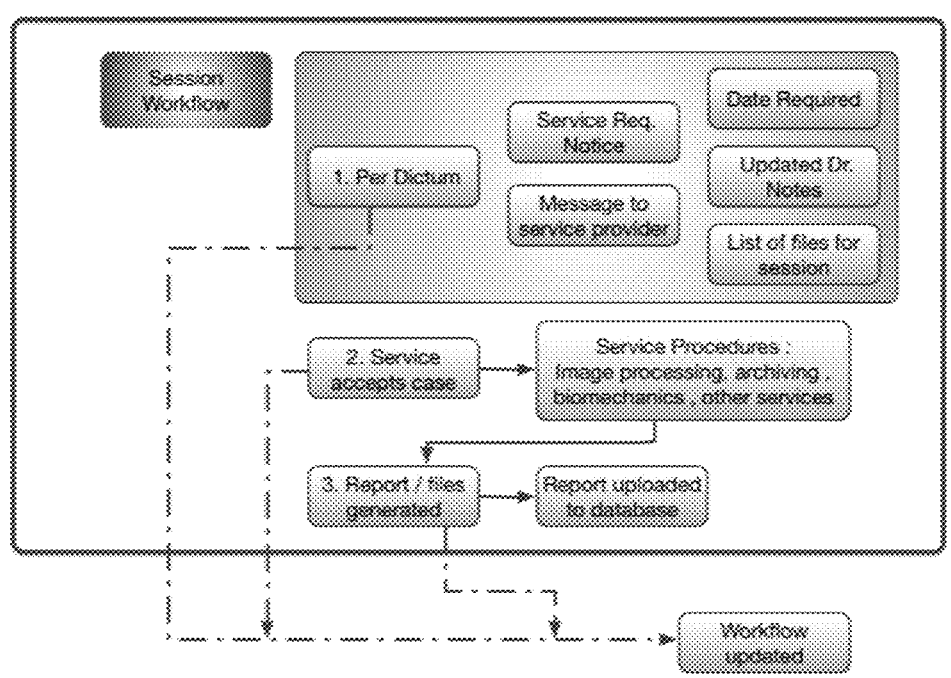
FIG. 10 illustrates the session workflow including per dictum, service engagement, report generation, and database and workflow updates.
Figure 11:
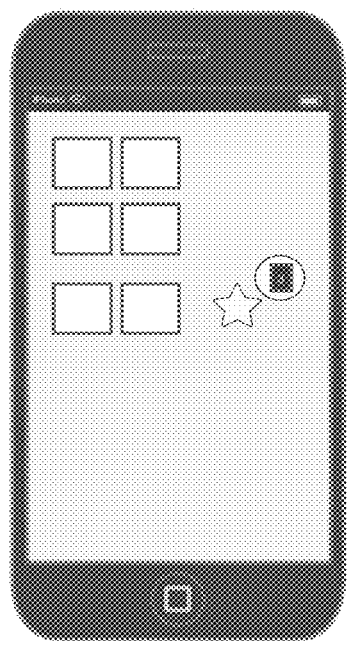
FIG. 11 illustrates a smart phone with a icon and visual notification of results to download and or read.
Figure 12:
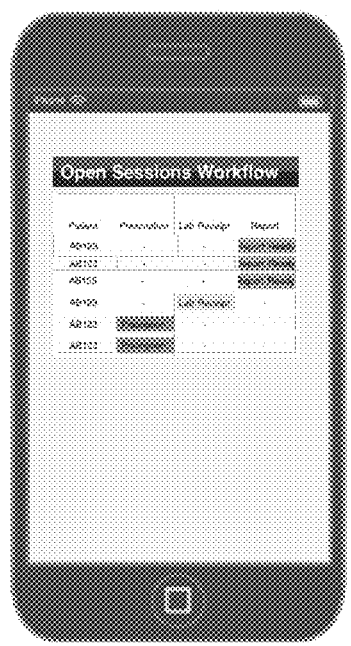
FIG. 12 illustrates a workflow progression on a smartphone that indicates the progress of various patient files, showing updates from a clinical support database.

In one embodiment, completing a clinical session FIG. 10, would initiate a management workflow and upload a session to one or more databases. Uploading a session would include encrypting files to assure privacy and security of sensitive data. A workflow as part of the presentation layer FIG. 12, enables a clinician to monitor a session or sessions progress described by a per dictum and associated with procedure codes, as well as for the coordination with a third party clinician or technical service provider, and to also ensure delivery of workflow enabled reports to appropriate parties. Workflows without a complete service per dictum will end automatically, for instance with the storage of an image or data to the appropriate database and its subsequent verification notice. Such notice may be required for medical/legal reasons as opposed to clinical treatment. Many sessions will require third party actions and report generation as part of the workflow. Accordingly there are also associated billing transactions. In an open session, an imaging session for instance may require third party comments or reports. Once a session has been started, it is logged in to the database and if a third party is requested to participate, then the workflow is tracked and the active session kept in the log until closed. A database logged session may require multiple clinical or laboratory sessions prior to completing and reporting. Updates allow the session changes to notify the clinician. A service requirement notice includes a date required notice and notification FIG. 11, such as an email to the service provider, the clinical notes, and list of attached files or links to their database location. Its function is to advise a service provider of the presence of a session to review. The session would remain active in the workflow until acknowledged by the service provider, such as a biomechanics lab 260 that might manage video processing, or an imaging lab service 240 or transcription service 250 that might provide post processing service for classifying skin images and all tasks are completed including review by the prescribing clinician 210. The third party clinician 230, laboratory 240, or session service provider would be in receipt of a file notice from the clinician 210 or referring clinic 220 through a clinical support database 300, this would in turn update workflow metadata FIG. 12. A file reader would open a file associated instruction read notice to download and decrypt from the database, file download would retrieve the database series, and a report template would generate/publish report and encrypt for the report upload and create a notice to clinical parties associated with the session and further update the workflow and metadata.

Third party services would be listed in a support services database 360, including a clinician database 361, a laboratory services database 362, and support services database 363 all connected to the clinical support database and its features, and further enabled with security management. Additional backup services 350 such as cloud support, would enable a redundant database backup 351 and historical database backup 352, to enable mobile device security and patient privacy, especially to avoid keeping substantial data on the mobile device.

In one embodiment the media is mapped to a database of procedures linked to per dictum and session data, which is related to the clinician data, the patient data, the session data, the historical context, the service provider, the probabilistic data such as predictive interpretation 321, and the workflow metadata would be also stored for archive and retrieval. Metadata can be adjusted based on actions, procedures, diagnoses, reports and all could impact the workflow and communications as part of routine database management. This would include indexing, querying, uploading, categorizing and downloading of session data. Further there would be a capability to export data and metadata into an external protocol such as DICOM. In such a data export case the non-conforming data such as predictive data, could be encoded into reference data attached to an external protocol data object.

Further, the metadata and documents associated with session data, can be broken down into sub-sets of data, and classified into a database based on non workflow characterization, such as by probability, or interpretation allowing rapid querying by multiple associations. An associative array may further allow database queries on the basis of key/value pairs in association with session data. Such association and classification can be used to determine what is prioritized in the presentation layer clinical report display, and subsequently how it is displayed to a clinician.

Design of a Clinical System for Data Capture, Database Management and Reporting

Figure 13:
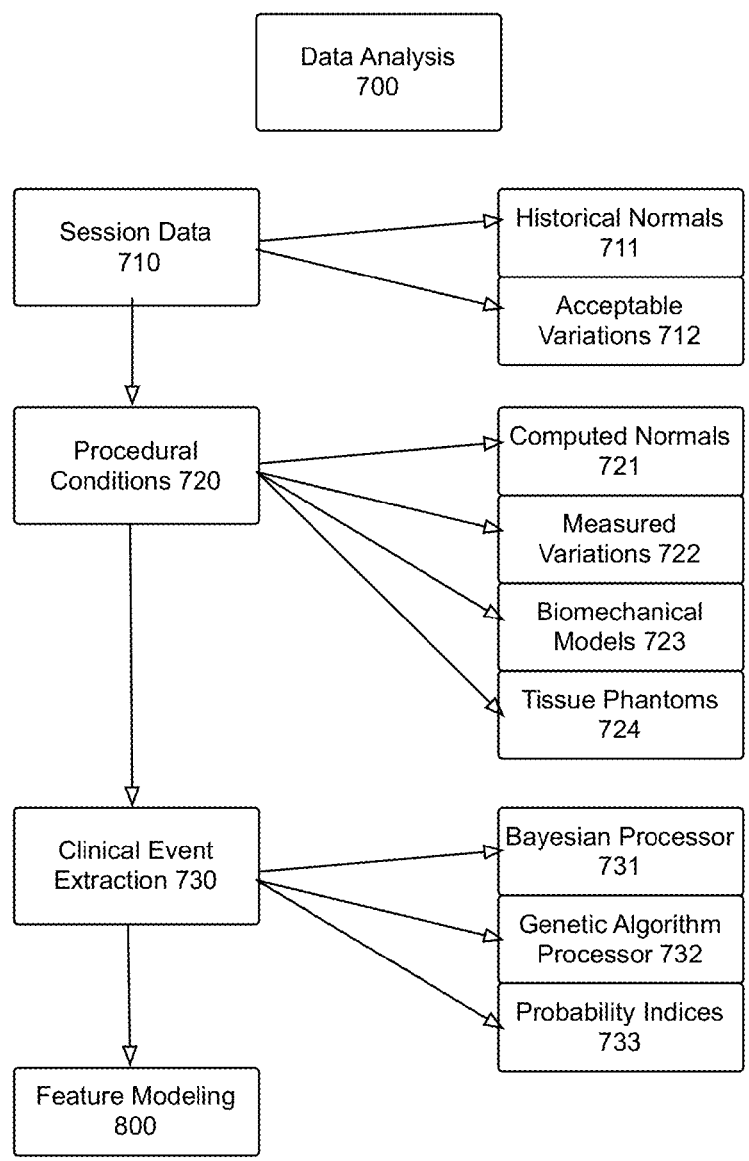
FIG. 13 illustrates a data analysis for session data, procedural conditions, clinical events and modeling.
Figure 14:
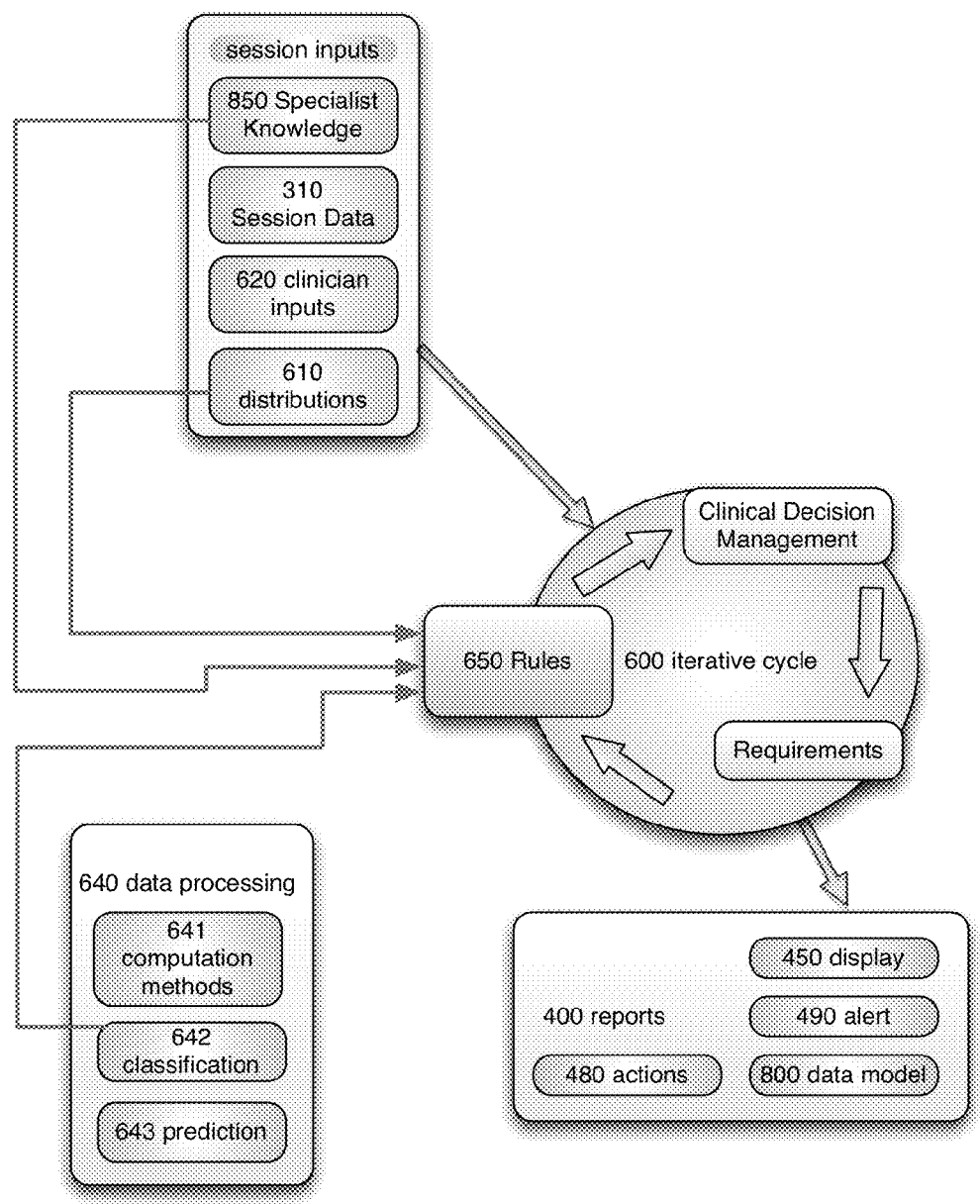
FIG. 14 illustrates an analysis system the enables the database to use iterative learning in processing and storage of session data and metadata.
Figure 15:
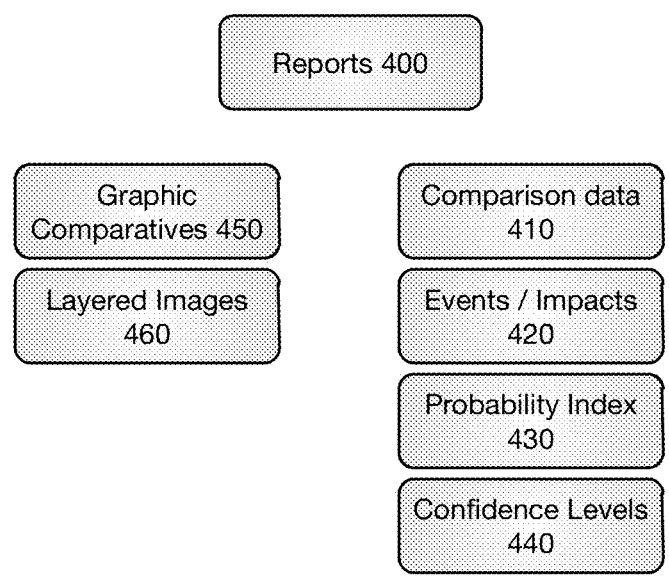
FIG. 15 illustrates a document reporting system that uses graphics, and indices to create reports for clinicians.
Figure 17:
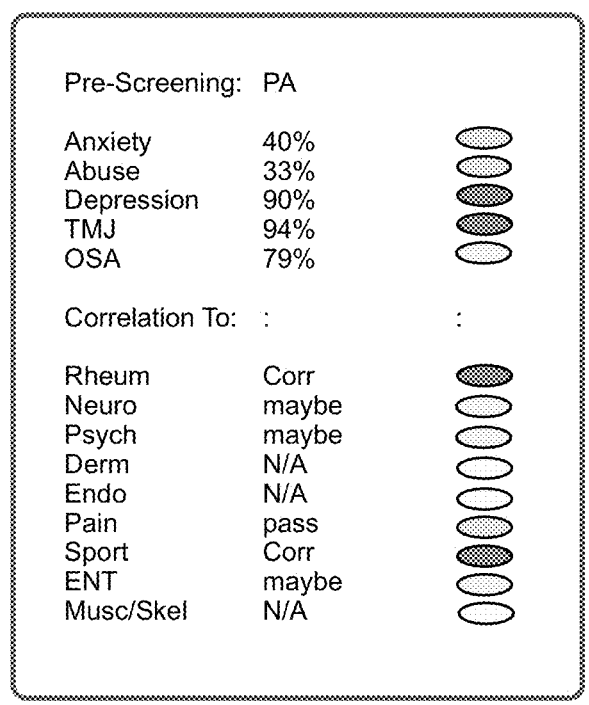
FIG. 17 illustrates the presentation layer showing a probability analysis to allow for direct interface to the data, or allowing the clinician to change the weighting of certain parameters or to force the system to recalculate the probability of other conditions.

In one embodiment the invention is a combination of data processing and data mining techniques to be used in further combination with smartphone, digital camera or the like 111, in a configuration to allow for rapid processing of data including the per dictum of a clinician. In some situations, the performance of a clinical system might be tied to its predicted conditions 321, and in an iterative system FIG. 14 by use of an analysis and processing method FIG. 13, so could provide data to verify after processing or to provide in advance of further analysis a means to measure changes that infer non specifically clinically useful information about some condition such as a weighted analysis that displays a probability of the involvement of certain conditions. Such probability analysis can be presented in a presentation layer screen format for the clinician and allow for direct interface to the data, such as the clinician overriding a probability analysis based on the apriori knowledge of the case, or allowing the clinician to change the weighting of certain parameters to force the system to recalculate the probability of other conditions FIG. 17. Such a probabilistic, iterative interface can be enabled with the capability of displaying data in multiple dimensions, such as spectral filtering of images, or simulation of biomechanical functions.

The inventions require three aspects to analyzing data 700. First is the identification of session data 710. Second is following and measuring of session procedural conditions 720. Third is the extraction from session data of events 730 that can also be used to correlate relevance in a knowledge based context in the clinical support database 300.

Interpretation of Critical Data

Modeling

A number of algorithms using different methods are used to represent the states of a data system and predict change. In a clinical data capture environment this can include data such as biomechanical data such as video tracking, and skin analysis such as wound and lesion tracking. In these cases there is a variable time between data points or images and or clinical sessions and one or more data or image points as may be tracked or interpreted in an iterative system that creates predictive data and its subsequent presentation layer, including where optimal, simulation or other method of comparing data to the clinician.

Indicators Versus Actual Problem

Predictive algorithms in an artificial neural network process can be used as signs of a situation to establish reference data 312 where measurement of the actual data is not practical or available. For instance Bayesian and genetic and rule based analysis running in parallel would provide robust and scalable indicators of the conditional status of data in an artificial neural network that supports clinical data collection and related database and post processing functions.

User defined parameters may also be used to impart data into an artificial neural network process. The incorporation of existing data and knowledge can be made using a priori knowledge of the relationships between clinical events and their impacts 420, such that a user interface presentation layer might display. For instance, an artificial neural network is a non knowledge-based adaptive system that uses a form of artificial intelligence, that allows the systems to learn from past experiences/examples and recognizes patterns in information. The inputs to the artificial neural network include the Bayesian data, raw data and iterative data, and these may be used to specify the classification and registration of data to a database or data table.

Bayesian Knowledge

A Bayesian knowledge based representation can manage a set of variables and their probabilistic relationships between situation and signs, and it is used as a processor to compute the probabilities of the presence of the possible situations given their signs. The conditional probabilities in primary analysis are singular and represent the probability of a situation given the occurrence of signs. In one embodiment, to reduce interpretive errors, combined conditions are used in weighting for secondary analysis as may be presented in the screen format. This can be a robust tool to help compute the probability of an event with frequently updated data. The presentation layer can display processes probabilities as new data is presented. It uses the knowledge and conclusions of experts in the form of probabilities, and leads to decision support as new information is available as it is based on unbiased probabilities. However it is used in situations where specific use cases can be defined as P(A|B) being the probability of A under the condition B as would be well known to one skilled in the art.

Iterative Data

Posterior probability is another common method of integrating data in a learning context that can update the presentation layer. The posterior probability distribution of one variable given the value of another can be calculated by multiplying the prior probability distribution by the likelihood function and dividing by the normalizing constant commonly written as follows:

$$f_{X|Y} = y^{(x)} = \frac{fx^{(x)} L_{X|Y=y^{(x)}}}{\int_{-\infty}^{\infty} fx^{(x)} L_{X|Y=y^{(x)}} dx}$$

which gives the posterior probability density function for a random variable X given the data Y=y, where:
 fx$^{(x)}$ is the prior density of X,
 $L_{X|Y}$=y$^{(x)}$=$f_{Y|X}$=x$^{(y)}$ is the likelihood function as a function of x,
 $\int_{-\infty}^{\infty}$fx$^{(x)}$$L_{X|Y}$=y$^{(x)}$ dx is the normalizing constant, and
 $f_{X|Y}$=y$^{(x)}$ is the posterior density of X given the data Y=y, as would be well known to one skilled in the art.

Iterative functions such as posterior probability density and the conditional probabilities can be combined into a cumulative distribution function 610 that provide weighted connections in an artificial neural network used to update the presentation layer. This can be in combination with clinician inputs 620. Used as a processor it consists of points of reference and weighted relationships in three layers: session inputs, results or possibilities from the iterative cycle 600, and data processing 640 to provide results to the presentation layer reports 400, based on the rules 650 and clinical decision management. In general a system becomes more efficient with known results for large amounts of data, which can overcome the limitations of a logical condition or Bayesian solution. In the preferred embodiment, the system will provide a method to further integrate data from a rule-based algorithm in order to capture knowledge of clinical domain experts into expressions that can be evaluated known as rules 650. In one embodiment, when enough of these rules have been compiled into a rule base, the current working knowledge in a session can be updated against the rule base by chaining rules together until a conclusion is reached. This will provide the advantages of easily stored data, large amounts of information and rules which will help to clarify the logic used in the decision-making process with reference data 312, and elimination of fully customized program systems while still providing input from experts.

The output of the iterative cycle is designed to update the presentation layer with reports that include the display of processing results and graphic comparatives 450, alerts when certain rule criteria have been met 490, and an interface to respond to reports with actions 480. Real time data processing 640, can take advantage of the data analysis methods to expedite computation methods 641 and classification of data 642 and create a predictive analysis 643 especially as might be used in automated screening questionnaires for pre-screening patients. Presentation reports can further include layered images to allow for rapid review of an image timeline, and the impacts on those images of other data by the variance of rules. The presentation layer can also include probabilities or confidence levels FIG. 17.

Genetic Algorithms

Yet further, predictive algorithms used as a processor in an artificial neural network process can be further augmented by genetic algorithms in a non-knowledge based environment that continuously rearranges to form different re-combinations that my better represent the patterns in data than in the prior solutions, and would also serve to update the presentation layer.

In the genetic algorithm, a collection of binary strings which encode solutions to an optimization problem, that evolves toward better solutions where the fitness of every solution to provide useful data in the collection is continuously evaluated, multiple solutions are selected from the current population (based on their fitness), and patterns are used to form a new collection. The new collection is then used in the next iteration of the algorithm. The genetic algorithm requires a representation of the solution including expected behavior, physical qualities and a fitness function to evaluate the solution domain. A standard representation of the solution is as a bit array. This is convenient as the arrays are easily correlated due to their fixed size. The fitness function is a correlation of the expected data to the real data, and represents the quality solution. The fitness of the solution is the sum of correlation values of all solutions in the collection. This advantage to the artificial neural network process provides a robust iterative process to produce an optimal solution. The fitness function determines the good solutions and the solutions that can be eliminated and can process incomplete data by making educated guesses about missing data. This improves with every use due to adaptive system learning and provides an added benefit that it does not require large databases to store outcome data with the associated probabilities. Probability based solutions to clinical diagnostics and interpretation can be used to improve the communication within a workflow process, the correlation of data in a database, or the post processing of data based on such things an image correlation models and normalizing, registration and rectification of data as could be used to change the presentation of data in the presentation layer or to share such data with other clinicians to compare iterative and adaptive results from different clinical experiences.

Figure 18:
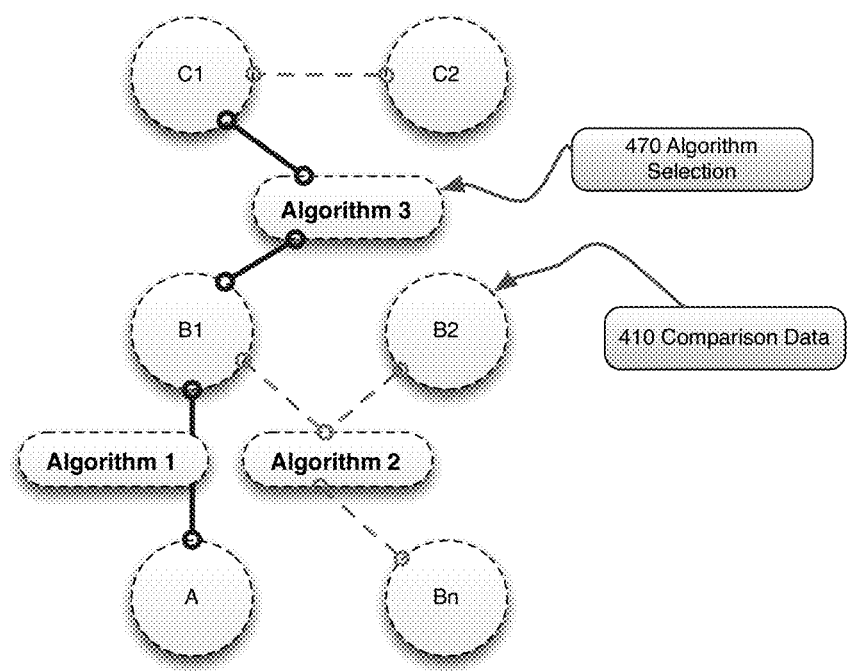
FIG. 18 illustrates a presentation layer that enables the choice of a processing algorithm for report generation.

In one embodiment of the system, the analysis of cause and effect in the probabilistic network is where clinical procedures and symptoms are evaluated in context of their relationships with patient specific data. A system based on this logic will attempt to trace a path from signs all the way to classification, using probability to determine the best fit, FIG. 18. A default algorithm selection 670 can be viewed and modified to see comparison data through feature modeling 800. Advantages of this are the modeled progression of a situation over time and the interaction between states. A root cause analysis is only valued when it is put in context. Traditional models might not be able to present useful data if an event is measured without it being in context. Apriori knowledge including clinical interpretation of screening and examination 620 and data can be used in an iterative cycle 600 to qualify the relationship between absolute variations in data and their relative changes to either patient specific data or other measures and indicators. This may include computational models in the data analysis 700, that represents a reference state, such as a biomechanical model 723, or a tissue phantom 724 both which can exist as virtual objects such as mathematical models or as two or three dimensional representation of a mathematical model in the presentation layer. Further data from sensors such as images from digital cameras, can be used in reference to modeled data, and allow for enhancement by comparison or normalization to a apriori determined reference data.

In one embodiment of the invention the presentation layer can include an interactive view of the algorithm 470 used and the weights of various steps in determining the outcome. The clinician would be able to adjust the weights or compare the results 410 to the presentation layer from various algorithms, FIG. 18.

One objective of the invention is to create reference calculations 721 as a form of metadata. The metadata is used to characterize the clinical data in reference to a procedure or other data that might contribute to measure the normal pattern of operations and interference, prior to a data capture series. The reference calculations or metadata pattern reference would subsequently be representative as a look up table in a relational database or reference algorithm of procedural conditions. Such a reference could be represented as a chart in the presentation layer on a clinical screening device where a clinician can input the perceived state of certain conditions.

One objective of the present invention is to provide a format for a mathematical model for data analysis 700 where a sequence of processes is used to establish the relevance of data to each specific use case and display these features in a presentation layer that enables a clinician to quickly see historical normals 711, acceptable variations 712, and as the session progresses, the conditions 720 as compared to the data measured at the various steps of session data. Data can be compared to computed normals for that patient 721, or variations from a prior session 722, or standard models such as a biomechanical model 723, or virtual tissue phantoms 724. This requires that there are established normal functions 711 and acceptable variations from a standard 712. This could include variations that are considered as clinically significant or events 730 that can be extracted from data as determined by a Bayesian processor 731, genetic algorithm processor 732, or probability indices 733. Prioritization of events or orthogonal relationships can have particular relevance to the interpretation of data as clinicians may deviate from a procedural sequence in order to enhance the diagnostic or informational post processing, which may impact the way data is presented in a database, or prioritized in a workflow.

In some cases, the orthogonal data metadata or images may be derived in pre processing of data, for instance if a application is running on a smart phone to characterize spectra from a skin lesion and include such models as independently or in combination, the ratio of probability distributions of frequency, amplitude or spatial frequency variations from normal 733. Measurement of ambient conditions such as accelerometer data noise in the system can also be used to validate if changes in data are subject to conditions that might skew the biomechanical data 723 to yield false readings, and this may form a part of the metadata, and further impact how files are stored in a database.

The method may further include two dimensional imaging such registering sensor data by an at least one processor; and comparing the first and the subsequent digital data on a section by section basis by the at least one processor, examples of such comparison including such as imaging an area of skin, where such registration and comparison represents a data set of spectral changes or optical density at specific spatial coordinates in the first digital data to allow later comparison to changes in subsequent digital data of the region of interest, or to a tissue phantom 724.

The method may further include comparing by the at least one processor, a number of ratios of respective radiant spectral intensity of a number of wavelengths or wavebands in a first optical data set, including normalizing a plurality of data sets including a normal frequency distribution. In such case the preprocessing and automated communications at the database could change the procedural protocol for the type of images required.

The method may further include establishing a subject specific baseline by the at least one processor which is specific to a subject; and wherein the normalizing is based at least in part on the subject specific baseline first data set and a plurality of sequential data sets, the sequential data or images sequentially captured at various times following a capture of the first digital data. The method may further include determining a number of differences in the dataset region of interest, as the region of interest appears between the normalized data sets including the first data set and the plurality of sequential data sets, by the at least one processor, as part of an analysis for the presentation layer. Display of the differences may include determining any changes of the data of interest between the normalized first data and the plurality of sequential data.

The system may further include generating a probability index 430 by the at least one processor based on a combination of distributed properties of a number of variables including a normalization, measuring and correcting for the total energy associated with a data set correction, a geometric or vector correlation, an optical spectroscopic correction, a signal to noise characterization, or a defined diagnostic protocol. Such a probability index would be useful to update a workflow or prioritize session data in a database or processing algorithm, and further update the presentation layer. The instructions may further cause the at least one processor to generate a digital model in the presentation layer that represents the subject or a region of the subject of interest in n dimensions based on multivariate data sets. The method may further include associating at least one of multivariate data or timeline data to the digital model with a geometric model that represents the subject of interest with a visible interface such as in two or three dimensions by the at least one processor.

Data set correction may further include correcting for frequency effects in the data set sample represented in at least the first data set which effects are due to interactions of multivariate data in a time domain sequence, and to cross reference and compare a number of derivatives. Correcting may include correcting for differences in time domain response to at least one of an excitation data set to an emission or imaging data set.

The method may further include registering each of a plurality of digital data sets of measured data from the subject, by the at least one processor, including the first digital data, based at least in part on a variation between data layer correlation in a temporal sequence of a plurality of digital datasets stored in a database, from the subject of interest and deriving information or diagnostic report data, and updating session data in a database.

The method may further include generating by the at least one processor an analysis comparison of layers in at least the first digital data as a histogram. The method may further include generating by the at least one processor a probability distribution of a sample being abnormal. Generating a probability distribution of a sample being abnormal or out of pattern may include generating the probability distribution of the sample being abnormal. Such analysis would depend on data stored in a historical database 352 and may include comparison to modeled reference data, 312, 723, 724. A probability distribution of a sample being abnormal may include generating the probability distribution with a probability index that weights at least some digital data according to at least one of a diagnostic value or a comparative amount of change between measured data. The instructions may further cause the at least one processor to store the digital data as a multi-layer file, including a first digital data layer that stores and at least a second digital data layer that stores metadata, such files being part of a clinical session protocol and associated with a work flow and database.

The instructions may further cause the at least one processor to reference in an image or data set at least one of frequency changes or energy density at specific coordinates in the first digital data set to allow later comparison to changes in a number of subsequent digital data sets of the region of interest. The instructions may further cause the at least one processor to compare a number of ratios of respective changes from the first digital data set or at least one subsequent digital data set, and create the appropriate sequence metadata.

The instructions may further cause the at least one processor to establish a subject specific baseline, normalized based at least in part on the subject specific baseline the first digital data set and a plurality of sequential digital data sets, the sequential digital data sets sequentially captured at various times following a acquisition of the first digital data set. The instructions may further cause the at least one processor to determine differences in the region of interest as the region of interest appears between the normalized digital data set including the first digital data and the plurality of sequential digital data set as part of an analysis. The instructions may further cause the at least one processor to determine changes of the region of interest as the region of interest appears between the digital data set as part of the determination of the differences in the region of interest as the region of interest appears between the normalized digital data set including the first digital data and the plurality of sequential digital data sets.

The instructions may further cause the at least one processor to correct for artifacts in the sample data set represented in at least the first digital image which effects are due to interactions of multivariate data in a defined time domain, and to cross by at least one of a digital model of sample data or other digital data to generate the digital two or three dimensional model of the data of interest 800. The instructions may further cause the at least one processor to correct for differences in priority orientation of at least one data set to display a representation of the datasets in an interface.

The instructions may further cause the at least one processor to generate an analysis comparison of layers in at least the first digital data as a histogram. The instructions may further cause the at least one processor to generate a probability distribution of a sample being abnormal. The instructions may further cause the at least one processor to generate the abnormal relationship of the data viewed within a probability index that weights at least some digital data according to at least one of a diagnostic value or a comparative amount of spatial or spectral change.

In one embodiment of the system, a processor is used for clinical reporting and is used to ensure that data is secured without patient data compliance violations such as security and privacy risks. This includes encryption management, 344. This clinical reporting combined with contextual event processing with procedure codes and clinical protocols ensures and enables real-time identification and alerting of anomalies within clinical procedures and displayed by way of a presentation layer. Further database session data and metadata and or network activity, can include communications between various clinicians, laboratory technicians and support staff where patient data or patient related communications must be shared in a timely and secure manner. Such communication associated with a procedure may include text 124 messages, camera 121 based images, voice 128 messages, or other means as might be necessary and known to one skilled in the art.

An occurrence of an event requiring a patient risk management and communication and can further cause a clinician to initiate a procedure including the process of implementing decision management support, specialist referral, workflow analysis, risk interpretation with other empirical evidence and patient specific knowledge; and accepting or altering risks in an iterative process, updating metadata, updating patient clinical notes, correlation with clinical procedures, updating database session data, updating a workflow, initiation of a per dictum for services or other analysis and reporting functions as normal to one familiar with the art.

Predictive Models and Approximations

One objective of the invention is to provide a method for pattern classifications based on groups of measurements and observations in a manner that is not rigid, and to further provide a means of storing and searching for data and metadata in a database based on concepts, processes and procedures, including variations from normal and events. Classification requires that concepts have to have their logical process defined relative to the application domain and employed in order to define the concepts in terms of rules, restrictions, and properties including procedures, empirical data, communication between clinicians, diagnosis, changes over time and other clinically relevant inputs including iterative learning. It is another objective to the invention to apply classification of data analysis such that the presentation layer is obvious, intuitive and simple. This means presenting data in context with known and relative factors within a use case or clinical procedure and workflow. The result is to represent knowledge within heterogeneous domains based on reasoning and semantic dependencies rather than strict data relationships. To represent those relationships, hierarchical categorization or equality-relations may be applied. A categorization could distinguish between orthogonal, and non orthogonal groups data streams and related groups could inherit properties from their superordinates.

To extract knowledge by inferring relationships has real world consequences and must be given a degree of confidence. Such confidence can come from inputs from real world results and as such it is one objective of the invention to apply confidence levels 440 to various results based on their performance over time. For example, two algorithms might be used to represent change in data relationships, one that looks at probabilities over a short term and one over a long term. In order to say we have more knowledge about the reported changes, some clinically relevant event must be presented in correlation. For instance, a biomechanical movement path might display a difference in function represented by a change in the pattern of the data, after a clinical treatment. A short term analysis would be sensitive to the acute changes but not the change in pattern. The long term analysis could filter out an acute changes event, but be sensitive to the change in pattern. In another instance, a long term analysis of a skin lesion might take into consideration noted by a clinician in a patient record, that the patient had increased sun exposure, and the resultant system or data processing correction would be to reduce the consideration of optical spectra that would be impacted by the increase in melanin, and further how such data and metadata might be stored, searched and accessed in a database for consideration in further cases, or in a iterative clinical learning scenario. In this manner we may further report changes in a presentation layer, in two domains from a patient session or sessions, which are the short and long term changes and their clinical relevance based on normalizing to a model or on a comparison of data or results from other like patterns. From a first event some knowledge can be inferred and a pattern can be established for 0 order pattern recognition and confidence assignment and such patterns may be associated with data or metadata in a database.

The invention will now be described with reference to specific examples. It will be understood that the following examples are intended to describe embodiments of the invention and are not intended to limit the invention in any way.

EXAMPLES

Example 1

Documents Formats

The series of algorithms and their use to represent a clinical procedure, protocol or a standard analysis are a format of common structure for using clinical data for a predictive analysis or workflow, and stored in the clinical support database as an attachment to the patient files. It also represents the style for which a set of documents for such analysis can be performed. These documents may be in the form of images or formats for a class of clinical procedures. This further simplifies the task of creating and interpreting multiple procedural and sequence data inputs by providing a predefined set of options within which data can be reviewed.

Example 2

Data Display

In one embodiment the invention provides an analysis that can be used as a document graphic or multi dimensional computer graphic representation, and is stored in the clinical support database as an attachment to the patient files, whereby the sample data is processed using protocol appropriate interactions of the different algorithms indicating the basis, or root cause of the probability analysis, image correlation, image layers, time scale analysis, spatial and spectral analysis.

Example 3

Text Exchange

In one embodiment the invention allows a clinician to select a patient ID and send a text message to another clinician. The text message is stored in the clinical support database as an attachment to the patient files, and the receiving clinician receives a notification from the database that there is a patient related message waiting for their review. In this solution a text message is not saved to a smart phone, is secure, encrypted and stored in the history backups.

Example 4

Screening Data

In one embodiment the invention allows a patient to complete a pre-clinical screening consisting of questions that are presented and or modified by the database based on a probability analysis, either based on the screening for a specific condition, or by the patient answering positively to questions that suggest correlation to a specific condition.

Example 5

Three Dimensional Simulation

In one embodiment the invention can parse 2D image or video data to a 3D processor that based on a mathematical model can infer a 3D shape to a 2D data set for the purpose of enhancing a presentation layer to help interpret the original data.

It is obvious that the foregoing embodiments of the invention are examples and can be varied in many ways. Such present or future variations are not to be regarded as a departure from the spirit and scope of the invention, and all such modifications as would be obvious to one skilled in the art are intended to be included within the scope of the following claims.

I claim:

1. A processor-implemented method, comprising:
instantiating a mobile device clinical presentation layer on a mobile device, the clinical presentation layer in communication with and supported by a clinical support database via the mobile device, the presentation layer configured to collect clinical session data from at least one mobile device sensor and/or mobile device camera, the presentation layer configured to provide: (1) a user interface on a display screen of the mobile device, the user interface configured to receive user input, and (2) at least one of a data display, image simulation, and/or representation of clinical data on the display screen;
displaying, based on user input received via the user interface, at least one clinical protocol for a clinical session;
collecting clinical session data at the mobile device, the clinical session data including information from at least one mobile device sensor and/or mobile device camera, wherein the clinical session data enables comparative features for data comparison, based on a per dictum, including at least one from the list of text, photographic, video, audio and/or iteratively prompted data sets associated with a patient file, in a workflow series within a clinical database management system;
determining, using at least one processor, a relationship between clinical signs and classifications using probability analysis whereby the at least one processor uses the steps of identifying session data, correlating with historical normals or variations, comparing and measuring of session procedural conditions, and extracting events from session data using bayesian analysis, genetic algorithm analysis, or probability indices, to correlate clinical signs to measures in the clinical support database, and providing probability weighted data;
updating the presentation layer based on the probability weighted data, wherein variations from established normal functions determine how data and metadata are stored and searched for in a database and prepared for display by an algorithm that processes the data based on the comparison of short term analysis to long term analysis, where acceptable variations from a standard are compared to variations specified as orthogonal to normal, and wherein those orthogonal relationships are derived in preprocessing including at least one of probability distributions of frequency, amplitude or slope variations from normal, and updating the presentation layer with clinical session data, and wherein the processing of clinical session data results in an output used to update confidence levels;

displaying the updated confidence levels;

upon determining completion of the clinical session, encrypting the clinical session data and uploading the encrypted clinical session data from the mobile device to a secure server.

2. The processor-implemented method of claim 1, further comprising: modeling the progression of a clinical situation over time using an iterative process to update the presentation layer by providing weighted data based on session inputs, results of the iterative cycle, and data processing, to update the confidence levels.

3. The processor-implemented method of claim 2, further comprising: generating reports based on a rule based system, iterative cycle and clinical decision inputs, that define the presentation layer including, comparison, events, impacts, probability and confidence data.

4. The processor-implemented method of claim 1, wherein the mobile device includes an accelerometer and the clinical session data includes accelerometer data from the accelerometer.

5. A processor-implemented method, comprising:

instantiating a mobile device clinical presentation layer on a mobile device, the clinical presentation layer supported by a clinical support database in communication with the mobile device, the presentation layer configured to collect clinical session data from a mobile device accelerometer and a mobile device camera, the presentation layer configured to provide: (A) a user interface on a display screen of the mobile device, the user interface configured to receive user input, and (B) at least one of a data display, image simulation, and representation of clinical data on the display screen;

displaying, based on user input received via the user interface, at least one clinical protocol for a clinical session, the clinical protocol including image collection guidance;

collecting clinical session data via the mobile device, the clinical session data including (a) session ambient conditions data and (b) information from a mobile device accelerometer and a mobile device camera, the information from the mobile device accelerometer and mobile device camera includes image information obtained at a first position and image information obtained at a second position to provide an image file series, the collected clinical session data configured for data comparison, based on a per dictum, of the collected clinical session data including the image file series associated with a patient file, in a workflow series within a clinical database management system;

determining, using at least one processor, a relationship between clinical signs and classifications using probability analysis whereby the at least one processor identifies session data, correlates session data with historical normals or variations, compares and measures session procedural conditions, extracts events from session to compare clinical signs to measures in the clinical support database, and provides probability weighted data;

updating the mobile device clinical presentation layer based on the probability weighted data, wherein variations from established normal functions including session ambient conditions data determine how data and metadata are processed and displayed based on the comparison of short term analysis to long term analysis, where acceptable variations from a standard are compared to variations specified as orthogonal to normal, and updating the mobile device clinical presentation layer with clinical session data, and wherein the processing of clinical session data results in an output used to update and display confidence levels;

upon determining completion of the clinical session, encrypting the clinical session data; and uploading the encrypted clinical session data from the mobile device to a secure server.

6. The processor-implemented method of claim 5, further comprising:

processing respective radiant spectral intensity of a plurality of wavelengths in a first optical data set based on the image file series; and updating image collection guidance of the displayed clinical protocol based on the processed respective radiant spectral intensity of the plurality of wavelengths in the first optical data set based on the image file series.

7. The processor-implemented method of claim 6, wherein determining and comparing ratios of respective radiant spectral intensity includes normalization of a plurality of data sets.

8. The processor-implemented method of claim 7, wherein the normalization includes determining a normal frequency distribution.

* * * * *